United States Patent [19]

Spademan

[11] 4,338,934

[45] Jul. 13, 1982

[54] INTRAVASCULAR CATHETER APPARATUS

[76] Inventor: Richard G. Spademan, Box 6410, Incline Village, Nev. 89450

[21] Appl. No.: 122,362

[22] Filed: Feb. 19, 1980

[51] Int. Cl.$^3$ .......................... A61M 5/14; A61J 1/06
[52] U.S. Cl. .................................. 128/214.4; 128/221; 277/237 R
[58] Field of Search ................ 277/237 R; 128/214.4, 128/221, 348

[56] References Cited

U.S. PATENT DOCUMENTS

| 3,313,299 | 4/1967 | Spademan | 128/214.4 |
| 3,853,127 | 12/1974 | Spademan | 277/237 |
| 4,027,668 | 6/1977 | Dunn | 128/214.4 |

FOREIGN PATENT DOCUMENTS 2461723  7/1976  Fed. Rep. of Germany ... 128/214.4

*Primary Examiner*—Richard J. Johnson

[57] ABSTRACT

An intravascular catheter apparatus (1) is described comprising a hub (2), means forming a first passageway (4), a canula (3), a puncturing means (9), a sealing means (8) and a means forming a second passageway (5) with said sealing means (8) extending a predetermined distance into said second passageway (5) for closing a hole (17) left in said sealing means (8) upon the withdrawal of said puncturing means (9) therefrom in response to a contact with a member (15) inserted in the second passageway (5).

6 Claims, 5 Drawing Figures

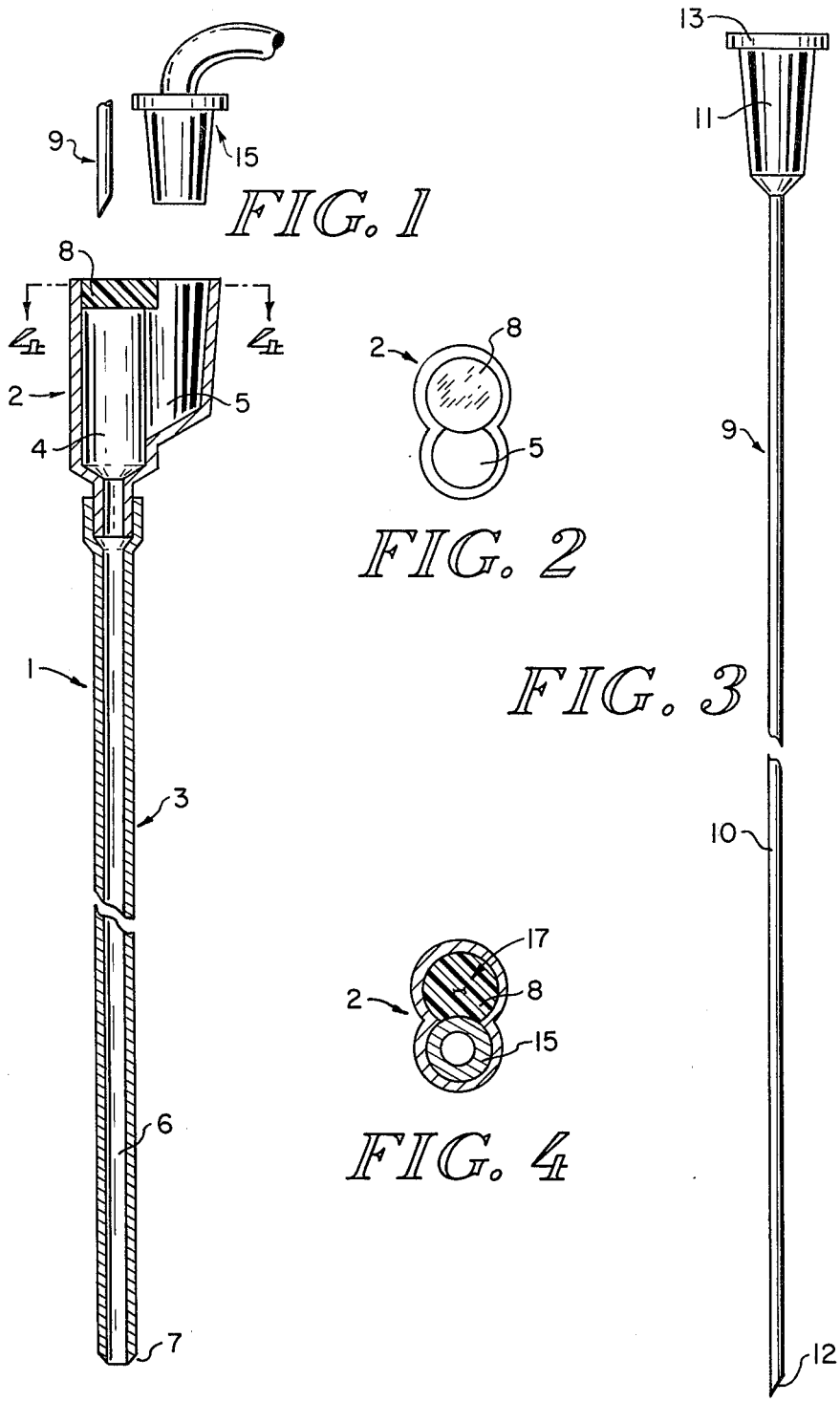

INTRAVASCULAR CATHETER APPARATUS

BACKGROUND OF THE INVENTION

The present invention relates to intravascular catheter apparatus in general and in particular to an intravascular catheter apparatus with a coaxial puncturing member, a sealing member for removably receiving the puncturing member and an integral infusion member for connecting an external infusion apparatus or the like to the catheter prior to its insertion in a body.

In applicant's U.S. Pat. No. 3,313,299 there is disclosed an intravascular catheter with a coaxial puncturing means. In the catheter disclosed there is provided a hub member. Extending from the hub member and a passageway located therein there is provided a canula. The puncturing means is provided for inserting the canula in a body. At the opposite end of the hub member there is provided a resilient sealing means. The sealing means is provided for removably receiving the puncturing means. Extending at an angle from the hub member and the passageway in the hub member there is provided an integral infusion connecting means forming a side passageway for connecting the catheter to an external infusion apparatus or the like.

In use, infusion apparatus is connected to the side passageway prior to the insertion of the canula in the body with the puncturing means. After the infusion apparatus is connected to the catheter and the canula is inserted in the body with the puncturing means, the puncturing means is removed from the canula, the hub member and the sealing means. Ordinarily, the sealing means, being a resilient member, closes tightly after the puncturing means is removed therefrom for preventing a flow of fluid from the catheter through the sealing means.

While fluid flow through the sealing means is generally prevented from occurring by the resilient nature of the sealing means, it has been found that when the puncturing means is left in the sealing means for a long period of time, as during shipping and storing of the catheters prior to their use, the material of the resilient sealing means sometimes becomes permanently deformed. When the sealing means becomes permanently deformed, a hole created in the sealing means by the puncturing means does not close or is easily forced open by internal pressures after the puncturing means is removed therefrom.

In applicant's U.S. Pat. No. 3,853,127, there is disclosed a plurality of embodiments of an improved elastic sealing member proposed for use in the intravascular catheter disclosed in applicant's U.S. Pat. No. 3,313,299.

In all of the embodiments disclosed in applicant's U.S. Pat. No. 3,853,127 there is provided a means for generating a nonuniform stress in an elastic sealing member in a plane substantially normal to the longitudinal axis of penetration of the sealing member by a puncturing means. The stress is generated by utilizing a sealing member having a first surface of a first configuration for sealing against a second surface having a second configuration. For use in or about a passageway having a walled surface configuration closely identical to that of a facing surface of a sealing member, a sleeve having a different surface configuration is used between the sealing member and the walled surface.

The fabrication of the catheters disclosed in applicant's U.S. Pat. No. 3,313,299 and applicant's U.S. Pat. No. 3,853,127 typically requires the use of molding equipment employing one or more slides. The fabrication of the unusual geometric shapes employed in the embodiments of the sealing member of applicant's U.S. Pat. No. 3,853,127 also requires relatively time consuming machining of the mold parts. Together, the use of molding apparatus requiring slides and the irregularly shaped curved surfaces of the molds, results in a relatively long cycle time, reduces mold capacity and increases part cost.

Still another disadvantage of prior known catheters of the type disclosed in applicant's prior patent involves the low friction nature of the material typically used in the fabrication of the hubs. Because of the low friction nature of the material used in the hubs, the retention of a member in the hubs which is typically used for connecting external infusion apparatus and the like to the catheter is often difficult. This is because there is a tendency for the connecting member to slide from the hub during normal handling.

SUMMARY OF THE INVENTION

In view of the foregoing, a principal object of the present invention is an intravascular catheter with coaxial puncturing means which employs features of applicant's prior U.S. Pat. Nos. 3,313,299 and 3,853,127.

Another object of the present invention is an intravascular catheter as described above having a hub with first and second interconnecting passageways disposed therein, a canula, puncturing means, and a sealing means. The canula extends from the hub and said first passageway. The puncturing means is provided for inserting the canula into a body. The sealing means is provided for removably receiving the puncturing means with a portion of the sealing means extending a predetermined distance into the second passageway. The portion of the sealing means which extends into the second passageway is provided for closing a hole left in the sealing means upon the withdrawal of the puncturing means therefrom. The hole is closed due to a compression of the sealing means in response to contact with a member inserted in the second passageway. The compressive forces between the sealing means and the member inserted in the second passageway also assists in retaining the member in the second passageway.

Another object of the present invention is an intravascular catheter as described above in which the first and second passageways are substantially parallel to each other.

Still another object of the present invention is a catheter as described above wherein said second passageway is adapted to receive a conventional infusion connecting means for compressing said sealing means. By placing the passageways in the hub of the intravascular catheter as described above in a parallel, side-by-side relationship wherein both passageways are in communication throughout substantially their entire length, the hub may be fabricated by conventional plastic injection molding apparatus techniques without employing a slide. This results in shorter cycle time, greater mold capacity and lower part cost.

BRIEF DESCRIPTION OF THE DRAWING

The above and other objects, features and advantages of the present invention, will become apparent from the following detailed description of the accompanying drawing in which:

FIG. 1 is a side cross sectional view of an intravascular catheter according to the present invention.

FIG. 2 is an end view of FIG. 1.

FIG. 3 is a side view of a puncturing means according to the present invention.

FIG. 4 is a cross sectional view taken along lines 4—4 of FIG. 1 with an external connecting means inserted in the intravascular catheter apparatus.

DETAILED DESCRIPTION OF THE DRAWING

Referring to FIGS. 1-4 there is provided in accordance with the present invention, an intravascular catheter designated generally as 1. In the catheter 1, there is provided a hub designated generally as 2 and a canula designated generally as 3, a first passageway 4 and a second passageway 5. The passageways 4 and 5 are generally cylindrically shaped, parallel and intersect such a way that they are in communication throughout a major portion of their length.

The canula 3 comprises a generally flexible hollow tubular member having an internal passageway 6 and a beveled end 7. The beveled end 7 is provided for inserting the canula in a body. The passageway 6 extends from one end of the passageway 4 and is provided to be generally in coaxial alignment with the axis of the passageway 4.

At the opposite end of the passageway 4 there is provided a sealing means comprising a sealing member 8. The sealing member 8 is provided for removably receiving a puncturing means designated generally as 9 and for sealing the passageway 4. It comprises a reseal plug typically fabricated from a resilient material. Its shape generally conforms to the shape of the passageway 4 and projects into the passageway 5 intersecting the passageway 4 as seen more clearly in FIG. 2.

The puncturing means 9 which may be solid or hollow is provided with a puncturing portion 10 and a head 11. The puncturing portion 10 is provided with a sharpened tip 12 for piercing a body when inserting the canula therein. The head 11 is provided with a flange 13 for facilitating the insertion and withdrawal of the puncturing means 9 from the catheter 1 and for interlocking with a syringe.

In practice, an intravascular catheter of the type described is generally supplied by the vendor thereof with the puncturing means 9 inserted through the sealing means 8, the hub 2 and the canula 3 in readiness for inserting the canula 3 in a body.

Prior to the insertion of the canula 3 in a body, an external infusion apparatus is often coupled thereto by the insertion of a conventional infusion apparatus connecting member and hose assembly 15 in the open end of the passageway 5. As the connecting member and hose assembly 15 is inserted in the open end of the passageway 5, it comes into contact with the sealing member 8. As the assembly 15 is inserted further into the passageway 5, the sealing member 8 is compressed by the assembly 15. After the assembly 15 is fully inserted in the passageway 5 and the canula 3 is inserted in the body, the puncturing means 9 is removed from the canula 3, hub 2 and sealing means 8.

After the puncturing means 9 is removed from the catheter 1, a hole, designated generally as 17 in FIG. 4, which may have been formed in the sealing means 8 by the puncturing means 9 is elongated and compressed. This elongation and compression of the hole 17 is caused by the pressure of the connecting assembly 15 inserted in the passageway 5 against the sealing means 8 and will close the hole 17.

While a preferred embodiment of the present invention is described, it is contemplated that modifications and changes to the embodiments described will undoubtably occur to those skilled in the art and may be made thereto without departing from the spirit and scope of the present invention. Accordingly, it is intended that the embodiments described be employed only for purposes of illustrating the present invention and that the scope of the present invention be determined solely by reference to claims hereinafter provided and their equivalents.

What is claimed is:

1. A catheter comprising:

a hub;

means forming a first passageway in said hub; a canula extending from said hub and communicating with said first passageway; a puncturing means for inserting said canula in a body; a sealing means in the first passageway for removably receiving said puncturing means, said sealing means including a solid member of resilient material and being of a size to permit the puncturing means to pierce and to extend through the solid member; and means forming a second passageway in said hub adjacent to and communicating with said first passageway with said solid member partially extending into the second passageway and being located in a position to be contacted and compressed by a connector member inserted in said second passageway for compressing said sealing means to close a hole formed therethrough by said puncturing means after the withdrawal of said puncturing means from said solid member.

2. A catheter according to claim 1 wherein said first and said second passageways are generally cylindrically shaped and open to each other along substantially all of one side thereof for permitting the fabrication thereof using injection molding technique without a slide.

3. A catheter according to claim 1 wherein said first and said second passageways are generally cylindrically shaped, the axes of said first passageway and said canula are colinear, the axis of said second passageway is parallel to the axis of said first passageway; and said first and said second passageways are in fluid communication with each other.

4. A catheter comprising: a hub having a pair of side-by-side passageways; a canula coupled to the hub and extending outwardly therefrom in fluid communication with said passageways; a solid, resilient sealing member in a first of the passageways, said sealing member being of a size to permit a puncturing means to pierce and extend through the member when the puncturing means extends through the first passageway and the canula, said sealing member extending partially into the second passageway and being engageable by a connector member inserted into the second passageway to cause the sealing member to be compressed and to close a hole formed by the puncturing means extending through the sealing member after removal of the puncturing means therefrom.

5. A catheter as set forth in claim 4, wherein the first and second passageways have a common side boundary.

6. A catheter as set forth in claim 4, wherein the passageways are generally cylindrical, said sealing means comprising a generally cylindrical plug extending into the first passageway and having an outer peripheral portion extending into the second passageway.

* * * * *